United States Defensive Publication [19] (H) [11] T988,010

Cunningham et al. [43] Nov. 6, 1979

[54] PROCESS FOR PREPARING $C_1$–$C_5$ ALKYL 5-(SUBSTITUTED-PHENOXY)-2-NITROBENZOATE

[75] Inventors: Theresa L. Cunningham, Jackson; Clifford E. Hunt, Somerset, both of N.J.

[73] Assignee: Mobil Oil Corporation, N.Y.

[21] Appl. No.: 16,851

[22] Filed: Mar. 2, 1979

Related U.S. Application Data

[63] Continuation-in-part of Ser. No. 903,275, May 5, 1978, abandoned.

[51] Int. Cl.[2] ..... C07C 79/46

[52] U.S. Cl. ..... 560/21

[57] ABSTRACT

A process of preparing $C_1$–$C_5$ alkyl 5-(substituted-phenoxy)-2-nitrobenzoate such as a process for preparing methyl 5-(2′,4′-dichlorophenoxy)-2-nitrobenzoate by the coupling reaction of methyl 2-nitro-5-chlorobenzoate with the potassium salt of 2,4-dichlorophenol in dimethylformamide solvent to produce a reaction product mixture containing desired ester product and by-product potassium 5-(2′,4′-dichlorophenoxy)-2-nitrobenzoate. The yield of desired ester product is increased by a process that comprises reacting said reaction product mixture in situ, with methyl chloride at a pressure of about 440 mm. Hg. to about 50 psig., for between about 0.5 hour and about 4 hours, and at a temperature between about 75° C. and about 105° C. In a specific embodiment the process is carried out on bench scale at a temperature of between about 75° C. and about 100° C. and at a pressure of between about 10 psig. and about 50 psig. In another specific embodiment the process is carried out on plant scale at a temperature of between about 75° C. and about 105° C. and at a pressure of between about 440 mm. Hg. and about 760 mm. Hg.

5 Claims, No Sheets Drawing,

10 Pages Specification

The file of this unexamined application may be inspected and copies thereof may be purchased (849 O.G. 1221, Apr. 9, 1968).